United States Patent [19]

Inoue et al.

[11] Patent Number: 5,206,010
[45] Date of Patent: Apr. 27, 1993

[54] COMPOSITION FOR USE IN ORAL CAVITY

[75] Inventors: Takeshi Inoue; Kouji Maeda, both of Utsunomiya; Yasuteru Eguchi, Tokyo, all of Japan

[73] Assignee: KAO Corporation, Tokyo, Japan

[21] Appl. No.: 810,117

[22] Filed: Dec. 19, 1991

[30] Foreign Application Priority Data

Jan. 25, 1991 [JP] Japan .................. 3-23768

[51] Int. Cl.[5] .......................... A61K 7/16; A61K 9/16
[52] U.S. Cl. ........................ 424/49; 424/489
[58] Field of Search .................. 424/49-58, 424/489

[56] References Cited

U.S. PATENT DOCUMENTS

| | | | |
|---|---|---|---|
| 2,196,154 | 4/1940 | Schulerud | 424/49 |
| 3,803,301 | 4/1974 | Cordon et al. | 424/49 |
| 3,919,409 | 11/1975 | Perla et al. | 424/49 |
| 3,929,987 | 12/1975 | Colodney et al. | |
| 3,935,306 | 1/1976 | Roberts et al. | 424/49 |
| 3,955,942 | 5/1976 | Cordon et al. | 424/49 |
| 4,069,312 | 1/1978 | Mannara | 424/49 |
| 4,089,943 | 5/1978 | Roberts et al. | 424/49 |
| 4,102,992 | 7/1978 | Davis | 424/49 |
| 4,444,570 | 4/1984 | Barth et al. | 424/49 |
| 4,871,396 | 10/1989 | Tsujita et al. | 424/49 |

FOREIGN PATENT DOCUMENTS

| | | |
|---|---|---|
| 0269966 | 6/1988 | European Pat. Off. |
| 1055784 | 1/1967 | United Kingdom |
| 1284545 | 8/1972 | United Kingdom |
| 1383003 | 2/1975 | United Kingdom |
| 1383004 | 2/1975 | United Kingdom |
| 2106783 | 4/1983 | United Kingdom |
| 2144333 | 3/1985 | United Kingdom |

*Primary Examiner*—Shep K. Rose
*Attorney, Agent, or Firm*—Oblon, Spivak, McClelland, Maier & Neustadt

[57] ABSTRACT

A composition for use in the oral cavity comprising granules composed of a water-insoluble powders and a water-insoluble organic binder; and which granules have an apparent density of from 0.1 to 1.5 and collapse at a deformation rate of from 0.1 to 20% at a load of from 0.1 to 50 g per granule. The granules of the composition have a proper hardness so that the presence of the granules can be felt when used in the oral cavity. The composition makes users feel the cleaning effect of the composition by the tactual sense, while giving a pleasant feeling to users. The composition is particularly suitable as a dentifrice.

7 Claims, No Drawings

COMPOSITION FOR USE IN ORAL CAVITY

BACKGROUND OF THE INVENTION

1. Field of the Invention

This invention relates to a composition for use in the oral cavity. More particularly, it relates to a composition for use in the oral cavity comprising granules which have a specified apparent density and which collapse at predetermined deformation rate values so as to make users feel the cleaning effect of the composition by the tactual sense of the granule in the oral cavity. Moreover, the composition gives a pleasant feeling to users.

2. Description of the Background Art

Various compositions for use in the oral cavity are well known which comprise granules or granular materials. These granules or granular materials sometimes contain pharmaceutical ingredients such as drugs and enzymes, or they are incorporated into a composition to give the composition an attractive appearance. The size and hardness of granules are determined depending upon the purpose of use of the granules. For example, the size and hardness of granules may be so determined that users can realize, by tactual sense in the oral cavity, that the plaques on the teeth is being removed as the granules collapse to finally give no tactual sense of the granules. In another example, the granules are so designed that they do not give any tactually conceivable feel to users from the beginning, but only gives an aesthetic effect to the products to improve the appearance thereof.

In the processes of preparing such granules, a binder which includes a water-soluble material and a water-insoluble material has been used.

An example of the water-soluble material conventionally employed in the preparation of the granules is a water-soluble high molecular compound such as carboxymethylcellulose or methylcellulose. Granules prepared with such water-soluble binders, however, have a disadvantage in that their hardness significantly decreases when they are incorporated into a composition for use in the oral cavity such as a tooth paste which includes water. This causes collapse of the granules during the preparation process. Even when the granules can keep their granular shapes during the preparation process, the granules cannot be felt in the oral cavity, because the granules are softened due to contact with water. Accordingly, users cannot feel the presence of the granules and the cleaning effect thereof.

Examples of a preparation process using a water-insoluble material include a process disclosed in Japanese Laid-Open Patent Application Nos. 49-132249 and 50-81594 in which a wax is used as a water-insoluble binder to bind abrading agents for obtaining granules, and a process disclosed in Japanese Laid-Open patent Application No. 58-126806 in which abrasive agents are combined to form granules with ethylcellulose, which is water-insoluble but ethanol-soluble. However, granules prepared by these methods are still not satisfactory, because users cannot feel the granules very well in their oral cavities. When the amount of the binders is increased, the hardness of the granules increases, which makes users clearly feel the presence of the granules. In this case, however, collapsibility of the granules tends to be deteriorated, because a plastic deformation occurs instead of a brittle collapse when the amount of the binders increases. As a result, these granules give users an unpleasant feeling in that the granules stick to or are stuck between the teeth.

Thus, there has been a demand for a composition for use in the oral cavity which meets the following two requirements: gives a pleasant feeling to users; makes users feel the cleaning effect of the composition.

SUMMARY OF THE INVENTION

Under the above-mentioned circumstances, the present inventors have carried out intensive studies, and have found that a composition for use in the oral cavity, which includes a granule prepared by binding a water-insoluble powdery material and a water-insoluble organic binder, and having a specified apparent density and a physical property allowing the granule to collapse when the deformation rate reaches a specified value, has a high recognizability by the tactual sense in the oral cavity. Although the granule has a mechanical hardness making users feel the cleaning effect thereof, it keeps a proper collapsibility, thereby reducing the unpleasant feeling which would be given by the granule stuck to or stuck between teeth. This invention has been accomplished based upon these findings.

Accordingly, it is an object of the present invention to provide a composition for use in the oral cavity comprising granules composed of a water-insoluble powder, said powder comprising particles having an average diameter in the range of from 0.1 to 20 $\mu$m, and a water-insoluble organic binder; said granules having an apparent density of from 0.1 to 1.5 g/cc measured in accordance with JIS No. K 3362; said granules collapsing at a deformation rate of from 0.1 to 20% under a load of from 0.1 to 50 g per granule, said deformation rate being the change in particle size in the direction of compression measured for a single granule, placed between two hard surfaces, after being immersed in water, and then compressed by decreasing the clearance between said hard surfaces at a speed of from 0.1 to 10 mm per minute.

DETAILED DESCRIPTION OF THE INVENTION

Examples of water-insoluble powders which can be used as a starting material of a granule of this invention include calcium secondary phosphate, calcium tertiary phosphate, insoluble sodium metaphosphate, silica, aluminum hydroxide, magnesium phosphate, calcium carbonate, calcium pyrophosphate, zeolites, composite aluminosilicate, magnesium carbonate, red iron oxide, calcium sulfate, and mixtures thereof, among which zeolites in particular are preferred. The average diameter of the particles of these water-insoluble powders is preferably in the range of from 0.1 to 20 $\mu$m.

Examples of water-insoluble organic binders of this invention include oils and fats, and polymers which are water-insoluble and solvent-soluble, or become water-insoluble when reacted with a polyvalent metal; and thermoplastic resins and thermosetting resins, which are generally used as adhesive agents.

Examples of oils and fats which can be used as a water-insoluble organic binder include higher fatty acids and salts thereof such as waxes, paraffins, stearic acid, magnesium stearate and calcium stearate.

Examples of polymers which can be used as a water-insoluble organic binder include a homopolymer or a copolymer of compounds such as acrylic acid, acrylic acid esters, methacrylic acid, methacrylic acid esters, hydroxymethacrylic acid esters, styrene, vinyl acetate, vinyl pyrrolidone, maleic acid esters, methyl vinyl ether and α-olefins. Particularly preferred examples of such polymers include a homopolymer or a copolymer of compounds such as methyl acrylate, ethyl acrylate and butyl acrylate; a copolymer of butyl acrylate and methacrylic acid; a copolymer of vinyl acetate and one or more compounds selected from butyl acrylate, octyl acrylate, lauryl acrylate, stearyl acrylate and 2-ethylhexyl acrylate; a copolymer of styrene and one or more acrylates, such as methyl acrylate or octyl acrylate; a homopolymer or a copolymer of compounds such as methyl methacrylic acid and ethyl methacrylic acid; a copolymer of vinyl acetate and styrene; a copolymer of vinyl acetate and crotonic acid; a copolymer of vinyl pyrrolidone and vinyl acetate; a copolymer of vinyl pyrrolidone and styrene; and a copolymer of methyl vinyl ether and one or more compounds selected from ethyl maleate and butyl maleate. Further, other preferred examples of polymers which can be used as a water-insoluble organic binder include methylcellulose, carboxyethylhydroxyethylcellulose, carrageenan, xanthan gum, guar gum, tragacanth gum, alginates, acacia gum, gelatin, natural or modified starch, alkaline metal salts of carboxymethylcellulose; and derivatives of polyethylene glycol.

Examples of thermoplastic resins include emulsions of polymers and copolymers, such as polyvinyl acetate, copolymers of vinyl acetate and acrylic esters, copolymers of vinyl chloride and vinyl acetate, copolymers of ethylene and vinyl acetate, polyurethanes and polyvinyl butyral; aqueous solutions of gum arabic, casein, glue, gelatin, starch, dextrin, soybean protein, methylcellulose, ethylcellulose, hydroxyethylcellulose, serum albumin, polyvinyl methyl ether, polyvinyl pyrrolidone or polyvinyl alcohol; hot melts such as copolymers of ethylene and vinyl acetate, copolymers of vinyl acetate and ethylene, copolymers of ethylene and acrylic esters, phenoxy resins, polyamides such as nylon 11 or nylon 12 or copolymeric nylons, saturated polyesters, coumaroneindene resins, canadian balsam, shellac, rosin, oleoresins and waxes; instant adhesives such as cyanoacrylates; solvent solutions of polymers such as polyvinyl acetate, copolymers of vinyl acetate and acrylic esters, cellulose nitrate, copolymers of vinyl chloride and vinyl acetate, polyurethanes and polyvinyl butyral; and monomer cements such as of polystyrene, polymethyl methacrylate, polyvinyl chloride, polycarbonates, cellulose acetate and methyl methacrylate.

Examples of thermosetting resins include monomer cements of resins such as urea resins, melamine resins, condensation products of urea and melamine, phenol resins, resorcinol resins, furan resins, copolymeric resins of α-olefins and maleic anhydride and aqueous vinyl urethane resins; epoxy resins; unsaturated polyesters; thermosetting acrylic resins such as diacrylates, dimethacrylates, urethane diacrylates and modified acrylic resins; polyaromatic resins such as polyimides, polyamideimides and polybenzimidazoles; and polymer-alloy-type resins such as phenolic-epoxy resins, phenolic-polyvinyl butyral, phenolic-polyvinyl formal, phenolic-nitrile rubbers, phenolic-nylons, epoxyurethanes, epoxy-nylons, epoxy-nitrile rubbers, polyester-epoxy resins, phenolic-chloroprenes and epoxy-silicones.

In addition to the above, rubber latexes such as of natural rubbers, polyisobutylene rubbers, regenerated rubbers, polybutadiene rubbers, styrene-butadiene rubbers, chloroprene rubbers, nitrile rubbers, butyl rubbers, urethane rubbers and silicone rubbers can also be employed in the present invention.

In addition to the above-mentioned water-insoluble powders and water-insoluble binders, a granule of this invention may contain other components such as pharmaceutical agents, colorants, flavoring components and shaping agents which are generally used in dentifrices.

Examples of pharmaceutical agents which can be mixed in the granule include antiplasmin agents such as allantoins, epsilon aminocaproic acid and tranexamic acid; enzymes such as dextranase, amylase, protease, mutanase, lysozyme, bacteriolysis enzymes and lytic enzymes; alkali metal salts of monofluorophosphoric acid such as sodium monofluorophosphate and potassium monofluorophosphate; fluorides such as sodium fluoride, ammonium fluoride and stannous fluoride; polyol phosphate compounds such as salts of chlorohexydine, quaternary ammonium salts, dihydrocholesterol, salts of glycyrrhetinic acid, glycyrrhetinic acid and glycerophosphate; and tartar preventing agents such as chlorophyll, caropeptide, vitamins, sodium chloride, carbonates, organic acids, and water-soluble inorganic phosphate compounds.

Colorants which may optionally be mixed in the granule must be safe in terms of toxicity, and preferred examples thereof include titanium oxide, ultramarine, red iron oxide, and titanium mica.

The granules for use in the present invention can be prepared by known methods, such as rolling granulation, extruding granulation, compressing granulation, crushing granulation, stirring granulation, fluidized bed granulation, spray drying granulation and melting-solidifying granulation. The preparation method of the present granules, however, is not limited to them, and other conventional methods can be used.

The granule prepared by any one of the above-mentioned methods is required to have an apparent density of 0.1 to 1.5 g/cc when measured with an apparent density measuring device described in Japanese Industrial Standard (JIS) No. K 3362, and the preferred apparent density is from 0.3 to 1.0 g/cc. When the granule has an apparent density less than 0.1, the shape of the granule cannot be felt in the oral cavity. On the other hand, when the granule has an apparent density more than 1.5, the primary particles formed of granules tend to agglomerate to make hard particles which cause a disagreeable feeling on use.

Also, the granule of this invention is required to collapse at a deformation rate of from 0.1 to 20%, more preferably from 0.3 to 10% under a load of 0.1 to 50 g, more preferably from 0.5 to 10 g, per particle. Here, the deformation rate is defined to be a change in the particle size in the direction of compression when measured in the condition that a single particle of the granule is placed between two hard surfaces after being immersed in water, and is then compressed by decreasing the clearance between the two surfaces at a speed in the range of from 0.1 to 10 mm per minute. When the granule collapses by a load less than 0.1 g, the granule cannot be felt in the oral cavity. On the other hand, when the granule collapses only by a load more than 50 g, the granule is not only felt as an alien substance in the oral cavity, but also does not collapse at all by brushing, and consequently the enamel of the teeth might be damaged by the brushing.

It is preferred that the shape of the granule be spherical, but those granules whose particle shapes are not spherical are also suitable for use in the present invention. It is also preferred that the inside of the granule be a cavity or that the granule be porous. The term "granule" also means an agglomerate of granules whose particle shape is approximately spherical, a melt product of granules, or a mixture thereof.

It is preferred that the particle size or diameter of the granule be such that the granule passes through a 35-mesh sieve, but does not pass through a 200-mesh sieve, namely, the preferred particle size or diameter is in the range of from 75 to 500 μm.

The preferred amount of granules in the present composition is from 1 to 50 wt. %, more preferably from 3 to 30 wt. %. When the amount of granules is less than 1 wt. %, the effects of the present composition may not be satisfactorily obtained. On the other hand, when the amount of granules is in excess of 50 wt. %, the resulting composition tends to give an unpleasant feeling to users.

In addition to the above-described granules, other suitable components such as abrading agents, binders, viscosity modifiers, surface active agents, sweetening agents, antiseptic agents, and other various pharmaceutical components may be incorporated into the composition of the present invention.

The composition for use in the oral cavity according to the present invention can be prepared according to any known process and be used as, for instance, a dentifrice such as a tooth paste, a moistened dentifrice and a liquid dentifrice, a mouth washing agent, a troche, a chewing gum, a paste for the mouth, a massage cream for gingiva, a liquid mouth refreshing agent and a solid mouth refreshing agent.

Since the composition for use in the oral cavity according to the present invention includes a granule having a hardness that makes users feel the granule, users can feel the plaques on the teeth being removed, as the granule gradually collapses in the course of brushing. An unpleasant feeling of granules stuck to or stuck between the teeth is significantly reduced. The present composition therefore makes users clearly realize the cleaning effect of the composition, while giving a pleasant feeling to users.

This invention will now be explained more specifically with reference to the following Examples, which are given for illustration of this invention and are not intended to be limiting thereof.

EXAMPLE 1

An aqueous slurry containing 60 parts by weight of zeolite, 10 parts by weight of polystyrene latex, 2 parts by weight of titanium oxide, and 28 parts by weight of synthetic aluminum silicate was granulated with a spray drying granulation machine.

The granules thus obtained were spherical particles having smooth spherical surfaces, and 91 % thereof passed through a 35-mesh sieve, but didn't pass through a 200 mesh sieve.

EXAMPLE 2

An aqueous slurry containing 60 parts by weight of calcium hydrogen phosphate, 10 parts by weight of polyacrylic stearate dispersed in water, 2 parts by weight of titanium oxide, and 28 parts by weight of synthetic aluminum silicate was granulated with a spray drying granulation machine.

The granule thus obtained were spherical particles having smooth spherical surfaces, and 88% thereof passed through a 36-mesh sieve, but didn't pass through a 200 mesh sieve.

EXAMPLE 3

An aqueous slurry containing 60 parts by weight of zeolite, 5 parts by weight of wax, 5 parts by weight of calcium stearate, 1 part by weight of titanium oxide, 1 part by weight of ultramarine, and 28 parts by weight of synthetic aluminum silicate was granulated with a spray drying granulation machine.

The granules thus obtained were spherical particles having smooth spherical surfaces, and 87% thereof passed through a 35-mesh sieve, but didn't pass through a 200 mesh sieve.

COMPARATIVE EXAMPLE 1

An aqueous slurry containing 60 parts by weight of calcium diphosphate, 35 parts by weight of magnesium almuminum metasililicate and 7 parts by weight of carboxymethylcellulose was granulated with a spray drying granulation machine.

The granules thus obtained were spherical particles having smooth spherical surfaces, and 84% thereof passed through a 35-mesh sieve, but didn't pass through a 200 mesh sieve.

COMPARATIVE EXAMPLE 2

60 parts by weight of calcium diphosphate, 9 parts by weight of ethyl cellulose, and a proper amount of acetone were kneaded, and the resulting mixture was subjected to extruding granulation using an extruding granulation apparatus, thereby obtaining a granule.

The granules thus obtained were cylindrical columnar particles, and 78% thereof passed through a 35-mesh sieve, but didn't pass through a 200-mesh seive.

EXAMPLE 4

Granules obtained in Examples 1, 2, 3 and Comparative Examples 1, 2 were tested in accordance with the following methods to measure the apparent density of respective granules, and to evaluate the recognizability and tactual feeling of respective granules. The results are shown in Table 2.

Apparent Density of Granule

The apparatus density of respective granules was measured in accordance with the procedure defined by the Japanese Industrial Standard (JIS) No. K 3362 using an apparent density measuring device at a temperature of 20° C. and a relative humidity of 60%.

Collapse Characteristics

Respective granules were immersed in ion-exchanged water of 20° C. for 24 hours, and a single granule thereof maintained in the wet condition was placed between two hard parallel plates of a compression test apparatus obtainable on the commercial market. The single granule was then compressed by narrowing the clearance between the two plates at a speed of 1.0 mm per minute to measure the deformation rate of the granule when collapsed. The test was further repeated 9 times to obtain the mean value of ten measured deformation rates.

Recognizability and Tactual Feeling of Granule

Tooth pastes having the formulation shown in Table 1 were prepared by using the granules obtained in Examples 1, 2, 3 and Comparative Examples 1, 2, respectively. The above-obtained tooth pastes were allowed to stand at room temperature for one week to stabilize the flavoring agents of the tooth pastes. After that, 20 panelists used the tooth pastes to evaluate them in terms of the recognizability and tactual feeling of each tooth paste in accordance with the criteria described below. The panelists used conventional toothbrushes having fibers whose tips are rounded off. The results are shown in Table 2, in which the results are shown by the number of panelists.

Recognizability of Granules (1) The presence of granule felt until brushing was finished.
(2) The presence of granule felt at the beginning of brushing, but it became impossible to feel the presence of granule in the course of brushing.
(3) The presence of granule not felt at all.

Tactual Feeling of Granules (1) No unpleasant feeling which would be given by granules stuck to or stuck between the teeth.
(2) Almost no unpleasant feeling.
(3) Slight unpleasant feeling.
(4) Unpleasant feeling.

TABLE 1

| Components | parts by weight (%) |
|---|---|
| Granule | 15.0 |
| Glycerin | 10.0 |
| Sorbitol | 30.0 |
| Sodium carboxymethylcellulose | 2.0 |
| Sodium laurylsulfate | 1.2 |
| Sodium saccharide | 0.1 |
| Methylparaben | 0.1 |
| Flavoring agents | 0.8 |
| Purified water | balance |
| Total | 100.0 |

TABLE 2

| Evaluation Items | | Examples | | | Comparative Examples | |
|---|---|---|---|---|---|---|
| | | 1 | 2 | 3 | 1 | 2 |
| Apparent Density of Granule (g/cc) | | 0.6 | 0.5 | 0.4 | 0.9 | 1.7 |
| Deformation Rate When Collapsed (%) | | 4 | 3 | 2 | 47 | 13 |
| Load When Collapsed (g) | | 7 | 9 | 12 | 1 | 3 |
| Recognition of Granule (Number of Panelists) | (1) | 13 | 15 | 12 | 1 | 4 |
| | (2) | 6 | 4 | 6 | 3 | 9 |
| | (3) | 1 | 1 | 2 | 16 | 7 |
| Tactual Feeling to Granule (Number of Panelists) | (1) | 9 | 7 | 10 | 7 | 1 |
| | (2) | 7 | 7 | 5 | 9 | 3 |
| | (3) | 2 | 4 | 4 | 4 | 7 |
| | (4) | 2 | 2 | 1 | 0 | 9 |

What is claimed is:

1. A composition for use in the oral cavity comprising granules composed of a water-insoluble powder, said powder comprising particles having an average diameter in the range of from 0.1 to 20 μm, and a water-insoluble organic binder; said granules having an apparent density of from 0.1 to 1.5 g/cc measured in accordance with JIS No. K 3361; said granules collapsing at a deformation rate of from 0.1 to 20% under a load of from 0.1 to 50 g per granule, said deformation rate being the change in particle size in the direction of compression measured for a single granule, placed between two hard surfaces after being immersed in water, and then compressed by decreasing the clearance between said hard surfaces at a speed of from 0.1 to 10 mm per minute.

2. The composition according to claim 1, wherein said granules have an apparent density of from 0.3 to 1.0 g/cc.

3. The composition according to claim 1, wherein said deformation rate is from 0.3 to 10%.

4. The composition according to claim 1, wherein said load applied to a granule, at the time of collapse, is in the range of from 0.5 to 10 g per granule.

5. The composition according to claim 1, wherein said granules have a particle size in the range of from 75 to 500 μm.

6. The composition according to claim 1, wherein said granules comprise from 1 to 50 wt % of the total weight of the composition.

7. The composition according to claim 1, wherein said composition is a toothpaste.

* * * * *

UNITED STATES PATENT AND TRADEMARK OFFICE
CERTIFICATE OF CORRECTION

PATENT NO. : 5,206,010
DATED : APRIL 27, 1993
INVENTOR(S) : TAKESHI INOUE ET AL

It is certified that error appears in the above-indentified patent and that said Letters Patent is hereby corrected as shown below:

Column 8, Claim 1, line 24, change "K 3361" to --K3362--.

Signed and Sealed this

Nineteenth Day of April, 1994

Attest:

BRUCE LEHMAN

*Attesting Officer*  *Commissioner of Patents and Trademarks*